US011006989B2

(12) United States Patent
Dooney et al.

(10) Patent No.: US 11,006,989 B2
(45) Date of Patent: *May 18, 2021

(54) METHOD AND SYSTEM FOR PROVIDING A SUTURE WRAP CERCLAGE

(71) Applicant: ARTHREX, INC., Naples, FL (US)

(72) Inventors: Thomas Dooney, Naples, FL (US); Laurence D. Higgins, Brookline, MA (US); Evan Lederman, Paradise Valley, AZ (US); Andrew Christian Petry, Naples, FL (US); Donald K. Shuler, Naples, FL (US)

(73) Assignee: ARTHREX, INC., Naples, FL (US)

( * ) Notice: Subject to any disclaimer, the term of this patent is extended or adjusted under 35 U.S.C. 154(b) by 246 days.

This patent is subject to a terminal disclaimer.

(21) Appl. No.: 16/431,921

(22) Filed: Jun. 5, 2019

(65) Prior Publication Data

US 2019/0282283 A1  Sep. 19, 2019

Related U.S. Application Data

(63) Continuation of application No. 15/365,510, filed on Nov. 30, 2016, now Pat. No. 10,314,628, which is a
(Continued)

(51) Int. Cl.
*A61B 17/82* (2006.01)
*A61B 17/04* (2006.01)
(Continued)

(52) U.S. Cl.
CPC .............. *A61B 17/82* (2013.01); *A61B 17/04* (2013.01); *A61B 17/06* (2013.01); *A61B 17/062* (2013.01);
(Continued)

(58) Field of Classification Search
CPC . A61B 17/04; A61B 17/1796; A61B 17/7053; A61B 17/82; A61B 17/823; A61B 17/826; A61B 17/842; A61B 17/8861; A61B 2017/0475; A61B 2017/0477; A61B 2017/048
See application file for complete search history.

(56) References Cited

U.S. PATENT DOCUMENTS 3,111,945 A    11/1963   Von Solbrig
3,469,573 A     9/1969   Florio
(Continued)

FOREIGN PATENT DOCUMENTS

WO         2015009808 A1     1/2015

OTHER PUBLICATIONS

International Preliminary Report on Patentability for International Application No. PCT/US2017/014924 dated Sep. 27, 2018.
(Continued)

*Primary Examiner* — Eric S Gibson
(74) *Attorney, Agent, or Firm* — Carlson, Gaskey & Olds, P.C.

(57) ABSTRACT

A method for providing a bone cerclage according to an exemplary aspect of the present disclosure includes, among other things, wrapping suture around a bone, tensioning the suture to tighten the suture relative to the bone, and securing the suture to the bone.

20 Claims, 11 Drawing Sheets

Related U.S. Application Data continuation-in-part of application No. 15/073,217, filed on Mar. 17, 2016, now Pat. No. 10,143,506.

(51) Int. Cl.
*A61B 17/06* (2006.01)
*A61B 17/062* (2006.01)
*A61B 17/88* (2006.01)
*A61B 17/84* (2006.01)

(52) U.S. Cl.
CPC ...... *A61B 17/06066* (2013.01); *A61B 17/842* (2013.01); *A61B 17/8861* (2013.01); *A61B 17/8869* (2013.01); *A61B 2017/06085* (2013.01)

(56) References Cited

U.S. PATENT DOCUMENTS

| | | | |
|---|---|---|---|
| 4,008,912 A * | 2/1977 | Kotov | B65D 63/12 289/1.2 |
| 4,119,091 A | 10/1978 | Partridge | |
| 4,146,022 A | 3/1979 | Johnson et al. | |
| 4,606,335 A | 8/1986 | Wedeen | |
| 4,643,178 A | 2/1987 | Nastari et al. | |
| 4,667,662 A | 5/1987 | Titone et al. | |
| 5,012,818 A | 5/1991 | Joishy | |
| 5,190,545 A | 3/1993 | Corsi et al. | |
| 5,250,053 A | 10/1993 | Snyder | |
| 5,318,566 A | 6/1994 | Miller | |
| 5,415,658 A | 5/1995 | Kilpela et al. | |
| 5,454,821 A | 10/1995 | Harm et al. | |
| 5,462,542 A | 10/1995 | Alesi, Jr. | |
| 5,501,688 A | 3/1996 | Whiteside et al. | |
| 5,540,703 A | 7/1996 | Barker, Jr. et al. | |
| 5,573,286 A * | 11/1996 | Rogozinski | A61B 17/82 289/1.2 |
| 5,573,542 A | 11/1996 | Stevens | |
| 5,628,756 A | 5/1997 | Barker, Jr. et al. | |
| 5,772,663 A | 6/1998 | Whiteside et al. | |
| 5,788,697 A | 8/1998 | Kilpela et al. | |
| 5,830,234 A | 11/1998 | Wojciechowicz et al. | |
| 5,851,209 A | 12/1998 | Kummer et al. | |
| 5,908,421 A | 6/1999 | Beger | |
| 6,093,190 A | 7/2000 | Mattchen | |
| 6,302,889 B1 | 10/2001 | Keller | |
| 6,368,326 B1 | 4/2002 | Dakin et al. | |
| 6,610,071 B1 * | 8/2003 | Cohn | A61B 17/06166 606/148 |
| 6,716,234 B2 | 4/2004 | Grafton et al. | |
| 7,207,090 B2 | 4/2007 | Mattchen | |
| 7,207,993 B1 * | 4/2007 | Baldwin | A61B 17/74 606/300 |
| 7,326,222 B2 * | 2/2008 | Dreyfuss | A61B 17/0469 606/103 |
| 8,162,997 B2 | 4/2012 | Struhl | |
| 8,231,626 B2 | 7/2012 | Hulliger et al. | |
| 8,298,247 B2 | 10/2012 | Sterrett et al. | |
| 8,337,534 B2 | 12/2012 | Celli et al. | |
| 8,460,295 B2 | 6/2013 | McClellan et al. | |
| 8,574,235 B2 | 11/2013 | Stone | |
| 8,672,969 B2 | 3/2014 | Stone et al. | |
| 8,984,720 B2 * | 3/2015 | Gephart | A61B 17/8861 24/69 R |
| 9,826,969 B2 * | 11/2017 | Larsen | A61B 17/0401 |
| 10,052,094 B2 * | 8/2018 | Spenciner | A61F 2/0811 |
| 10,136,886 B2 * | 11/2018 | Norton | A61B 17/0487 |
| 10,143,506 B2 * | 12/2018 | Dreyfuss | A61B 17/8861 |
| 10,314,628 B2 * | 6/2019 | Dooney | A61B 17/06066 |
| 2005/0033365 A1 * | 2/2005 | Courage | A61B 17/06109 606/232 |
| 2009/0306668 A1 | 12/2009 | Dell'Oca | |
| 2010/0211075 A1 | 8/2010 | Stone | |
| 2010/0249853 A1 | 9/2010 | Celli et al. | |
| 2012/0109129 A1 * | 5/2012 | Bernstein | A61B 17/823 606/74 |
| 2013/0018375 A1 | 1/2013 | Dell'Oca | |
| 2013/0096612 A1 | 4/2013 | Zajac et al. | |
| 2013/0239974 A1 | 9/2013 | O'Brien et al. | |
| 2014/0249530 A1 * | 9/2014 | Babikian | A61B 17/8861 606/74 |
| 2014/0257377 A1 | 9/2014 | Akutsu et al. | |
| 2015/0127003 A1 | 5/2015 | Songer et al. | |
| 2016/0183991 A1 | 6/2016 | Pratt | |
| 2017/0265917 A1 * | 9/2017 | Dreyfuss | A61B 17/06166 |
| 2017/0265918 A1 * | 9/2017 | Dooney | A61B 17/062 |
| 2019/0282283 A1 * | 9/2019 | Dooney | A61B 17/04 |

OTHER PUBLICATIONS

Y. M. Por, M. J. Lavin, "Techniques of intraocular lens suspension in the absence of capsular/zonular support", Survey of Ophthalmology, vol. 50, nr. 5, Sep.-Oct. 2005.

\* cited by examiner

METHOD AND SYSTEM FOR PROVIDING A SUTURE WRAP CERCLAGE

RELATED APPLICATIONS

This application is a continuation of prior U.S. application Ser. No. 15/365,510, filed Nov. 30, 2016, which is a continuation-in-part of prior U.S. application Ser. No. 15/073,217, filed Mar. 17, 2016 (now U.S. Pat. No. 10,143,506). The entirety of the '510 and '217 Applications are herein incorporated by reference.

BACKGROUND

This disclosure relates to a method and system for providing a bone cerclage.

Cerclages are used to maintain the relative position of fractured bone fragments to promote healing. While cerclages can be used relative to any fractured bone, they are commonly used to promote healing of femoral fractures. Femoral fractures are sometimes caused, for example, by traumatic injuries or as the result of an orthopedic procedure such as a hip replacement. A cerclage is used to fix fractured bone fragments relative to one another, which, again, promotes healing.

Known cerclages include materials such as cable (i.e., wire) or fabric, and are provided by wrapping the cable or fabric around a fractured bone a single time. After wrapping, the cable or fabric is then locked into place relative to the bone, such as with a plug or clip.

SUMMARY

A method for providing a bone cerclage according to an exemplary aspect of the present disclosure includes, among other things, wrapping suture around a bone, tensioning the suture to tighten the suture relative to the bone, and securing the suture to the bone.

In a further embodiment, the securing step includes securing the suture to the bone by tying a knot.

In a further embodiment, the securing step includes providing a sliding knot between a folded end of the suture and first and second free ends of the suture.

In a further embodiment, the sliding knot is at least partially pre-tied.

In a further embodiment, the tensioning step includes using a tensioner to pull the first and second ends relative to the sliding knot to tighten the suture.

In a further embodiment, the wrapping step includes wrapping the suture around the bone a first time in a first direction and a second time in a second direction opposite the first direction.

In a further embodiment, the suture is wrapped around the bone the first time by wrapping first and second free ends of the suture around the bone in the first direction.

In a further embodiment, the suture is wrapped around the bone the second time by providing wrapping the first and second free ends around the bone in the second direction.

In a further embodiment, the wrapping step includes using a suture passer to wrap the suture around the bone.

In a further embodiment, the suture passer is a needle.

In a further embodiment, the needle is a curved needle.

In a further embodiment, the needle includes a proximal end, a distal end, and a main body portion having a thickness tapering between the proximal end and the distal end.

In a further embodiment, a tip of needle is blunt.

In a further embodiment, a tip of the needle is sharpened.

In a further embodiment, the suture is a folded piece of suture.

A method for providing a bone cerclage according to another exemplary aspect of the present disclosure includes, among other things, wrapping a piece of suture around bone a first time in a first direction, wrapping the suture around bone a second time in a second direction opposite the first direction, tensioning the suture to tighten the suture relative to the bone, and securing the suture to the bone by tying a knot.

In a further embodiment, the securing step includes providing a sliding knot between a folded end of the suture and first and second free ends of the suture.

In a further embodiment, the tensioning step includes using a tensioner to pull the first and second ends relative to the sliding knot to tighten the suture.

In a further embodiment, the suture is wrapped around the bone the first time by wrapping first and second free ends of the suture around the bone in the first direction, and the suture is wrapped around the bone the second time by providing wrapping the first and second free ends around the bone in the second direction.

In a further embodiment, the wrapping step includes using a needle to wrap the suture around the bone.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

BRIEF DESCRIPTION OF THE DRAWINGS

The drawings can be briefly described as follows.

DETAILED DESCRIPTION

This disclosure details a method and system for providing a bone cerclage. The disclosed method includes wrapping a piece of material around a bone, and securing that material relative to the bone. The wrapped material provides a bone cerclage, which maintains the relative position of fractured bone fragments to promote healing.

Figures 1, 2, 3:
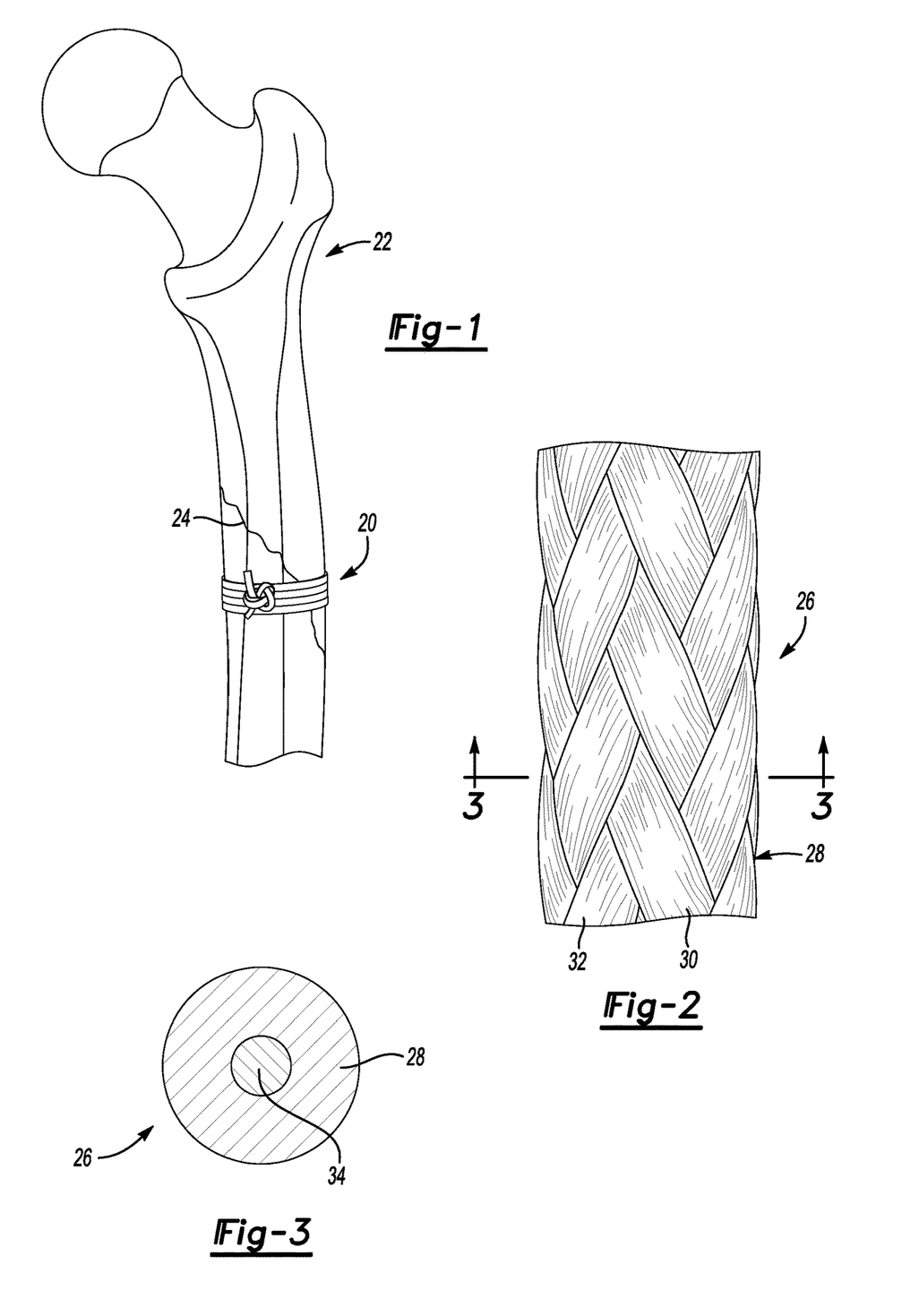
FIG. 1 illustrates a fractured bone provided with a suture wrap cerclage.
FIG. 2 is an external view of an example suture.
FIG. 3 is a cross-sectional view of the example suture, taken along line 3-3 of FIG. 2.

This disclosure includes several embodiments of a bone cerclage where the material providing the cerclage is suture. FIG. 1 illustrates a non-limiting example of a suture wrap cerclage 20 provided relative to a bone 22 with a fracture 24. In this example, the bone 22 is a femur. Femurs can fracture, for example, from a traumatic injury or as the result an orthopedic procedure, such as a hip replacement. The suture wrap cerclage 20 fixes the fractured fragments of the bone 22 relative to one another, which promotes healing. While specific reference is made to femurs, it should be understood that this disclosure is not limited to femoral fractures, and extends to other bones (such as the humerus).

Again, this disclosure includes several embodiments that relate to a method and system for providing a suture wrap cerclage. In one non-limiting example of the disclosed method, a surgeon, for example, may make use of a collection of components, referred to herein as a "system." Among other things, an example system includes suture 26, which forms the suture wrap cerclage 20.

An external view of an example suture 26 is illustrated in FIG. 2, and a cross-section is shown in FIG. 3. In this non-limiting example, the suture 26 is a high strength braided suture, such as Arthrex, Inc.'s FiberTape™.

In general, the suture 26 includes a multifilament cover 28 formed of a plurality of braided fibers of ultrahigh molecular weight polyethylene (UHMWPE) 30 and fibers of polyester 32. The cover 28 surrounds a core 34 formed of twisted fibers of ultrahigh molecular weight polyethylene (UHMWPE). While one example type of suture 26 is shown and described, it should be understood that other types of suture come within the scope of this disclosure.

Figures 4A, 4B:
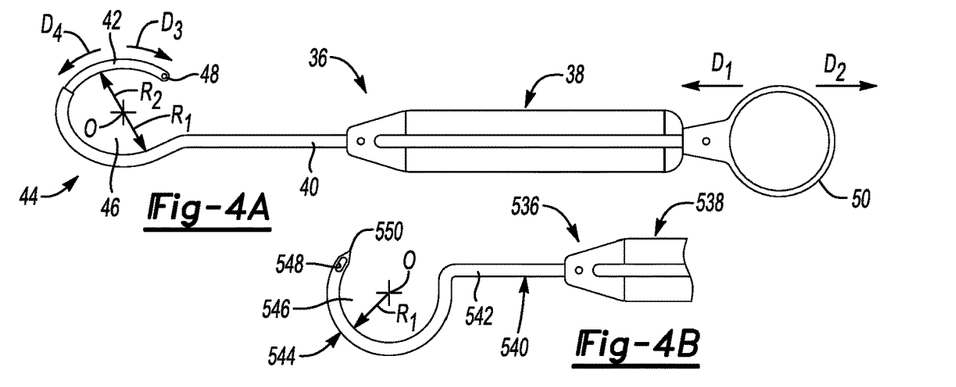
FIG. 4A illustrates a first example suture passer.
FIG. 4B illustrates a second example suture passer.

In addition to suture, the example system also includes a suture passer, such as the suture passer 36 illustrated in FIG. 4A. As shown in FIG. 4A, the suture passer 36 includes a handle 38, a cannula 40 extending distally from the handle 38, and a moveable suture carrier 42. In this example, the cannula 40 is substantially straight relative to the handle 38, and is curved at a distal end 44 to follow an expected contour of a bone (such as the bone 22 of FIG. 1). The distal end 44 follows a constant radius $R_1$ having an origin O in an expected bone location 46.

The moveable suture carrier 42 has an eyelet 48 for receiving suture, and is moveable relative to the cannula 40 in response to a corresponding movement of an actuation member 50 adjacent a proximal end of the handle 38. The suture carrier 42 has a curve adjacent the distal end 44 substantially following a constant radius $R_2$, which corresponds to the expected contour of a bone, and is substantially the same as the radius $R_1$. Further, in this example, the actuation member 50 is formed as a circular ring. It should be understood that the actuation member 50 could have other configurations.

In one example, the suture carrier 42 is integrally formed with the actuation member 50. In that case, the suture carrier-actuation member structure would be formed of a semi-rigid material, such as a relatively high strength plastic material, to allow the structure to pass through the cannula 40. In other examples, the suture carrier 42 and actuation member 50 may be formed separately from one another, and, in that case, can be formed of metallic material. This disclosure is not limited to any particular material type, however.

The actuation member 50 is slidable relative to the handle 38 in a distal direction $D_1$ and a proximal direction $D_2$. In response to movement of the actuation member 50 in the distal direction $D_1$, the suture carrier 42 is moveable in a direction $D_3$ away from a distal end 44 of the cannula 40. Likewise, in response to movement of the actuation member 50 in the proximal direction $D_2$, the suture carrier moves in a direction $D_4$ toward the distal end 44 of the cannula 40. Movement of the suture carrier 42 increases the ease of passing suture around a bone.

Another example suture passer is illustrated in FIG. 4B. The suture passer 536 in FIG. 4B is similar to the suture passer 36 in FIG. 4A, but the suture passer 536 does not include a moveable suture carrier 42 or the corresponding actuation member 50. The suture passer 536 also does not include a cannulated shaft.

In particular, the suture passer 536 includes a handle 538 and a shaft 540 projecting distally from the handle 538. The shaft 540 includes a substantially straight section 542 adjacent the handle 538, and a curved distal end 544. The distal end 544 is curved such that the distal end 544 follows a constant radius $R_1$ having an origin O in an expected bone location 546. The radius $R_1$ in this example corresponds to the expected contour of a bone. The distal end 544 includes an eyelet 548 for receiving suture. The eyelet 548 is provided adjacent a tip 550 of the distal end 544. The tip 550 in one example is sharpened to increase the ease of maneuvering the distal end 544 around bone. The tip 550 may be blunt in other examples.

Figure 5:
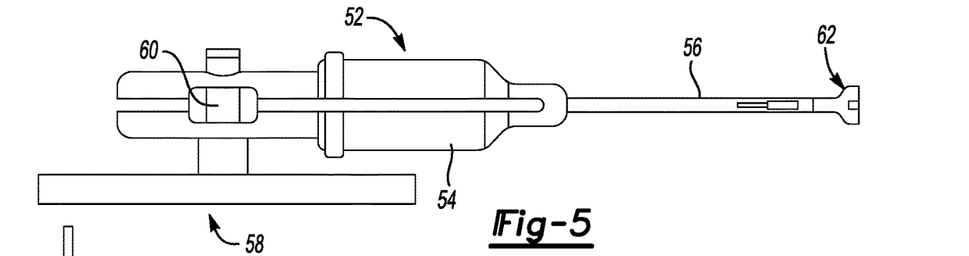
FIG. 5 illustrates an example tensioner.

The example system may further include a suture tensioner, such as the suture tensioner 52 illustrated in FIG. 5. A suture tensioner is a device that allows a surgeon, for example, to tension suture to an appropriate level, such as Arthrex's AR-1529 Suture Tensioner and Tensiometer.

In general, as illustrated in FIG. 5, the suture tensioner 52 includes a handle 54, a shaft 56, and an adjustment wheel 58. As will be further explained below, a free end of suture can be provided around a spool 60 connected to the adjustment wheel 58. The adjustment wheel 58 is then rotated to tension the suture. The suture tensioner 52 may optionally be used in combination with a spreader 62 (shown somewhat schematically), configured to keep adjacent free ends of suture spaced-apart from one another as the spool rotates. The suture tensioner 52 is not required in all examples, but its use may increase the overall tightness of the suture wrap cerclage 20 relative to a hand-tensioned cerclage. Its use may further increase efficiency and repeatability relative to hand-tensioning.

Figure 6:
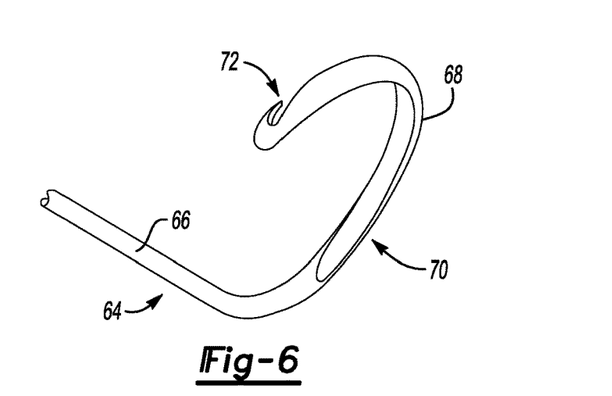
FIG. 6 illustrates another example suture passer.
Figures 7A, 7B:
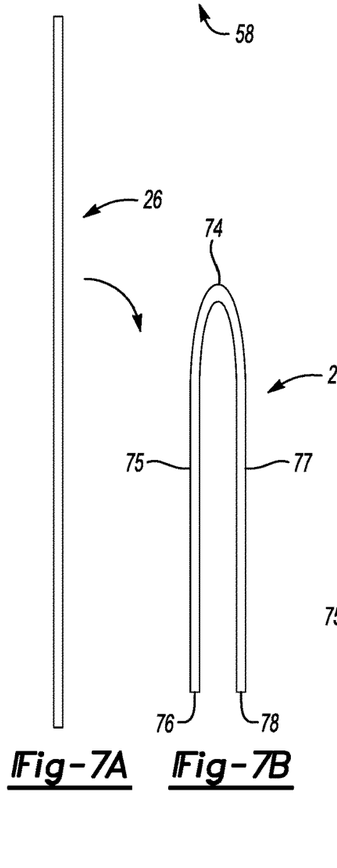
FIG. 7A illustrates a piece of suture.
FIG. 7B illustrates the piece of suture folded lengthwise.

While FIGS. 4A-4B illustrate two example suture passers 36, 536 other suture passers come within the scope of this disclosure. For instance, FIG. 6 illustrates a non-cannulated suture passer 64 having a substantially straight portion 66 and a curved portion 68 at a distal end 70. At an end of the curved portion 68, the suture passer 64 includes a suture retaining member 72, which in the FIG. 6 example is a notch. While a notch is shown, it should be understood that the suture passer 64 could be provided with another type of suture retainer, such as an eyelet.

A first example method of providing the suture wrap cerclage 20 will now be explained with reference to FIGS. 7A-16. In general, the method includes wrapping a suture around a bone at least twice, and then securing the suture to the bone. The method will be explained relative to the suture 26, suture passer 36, and the tensioner 52. While specific reference is made to these devices, it should be understood that other devices may be used. In particular, while FIGS. 7A-16 illustrate the suture passer 36, the suture passers 64, 536 could be used.

Figure 8:
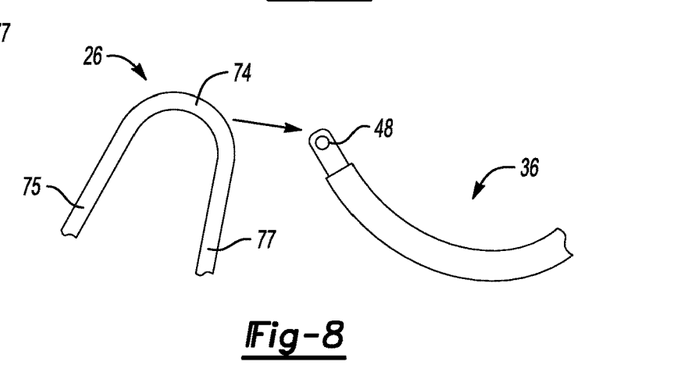
FIG. 8 illustrates an example method step of inserting a folded end of suture into an eyelet of a suture passer.

Initially, a piece of suture 26 (FIG. 7A) is folded substantially in half (FIG. 7B) about its length to provide a folded end 74, and first and second lengths 75, 77 between the folded end 74 and respective first and second free ends 76, 78. The folded end 74 is then placed in the eyelet 48 of the suture passer 36, as shown in FIG. 8.

Figure 9:
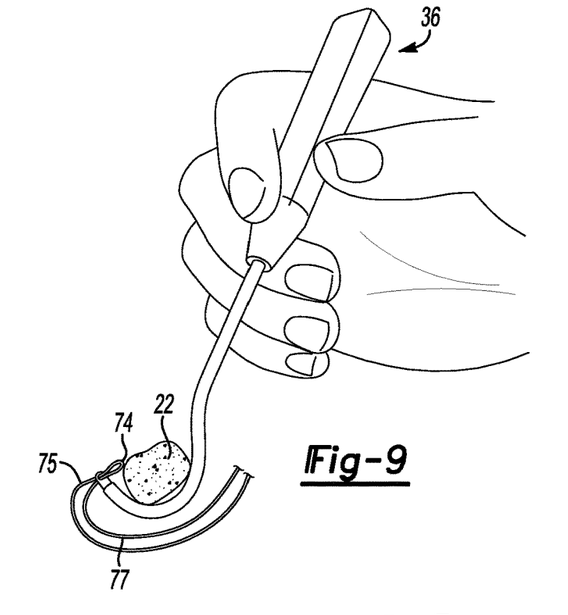
FIG. 9 illustrates an example method step of maneuvering the suture passer around a bone.
Figure 10:
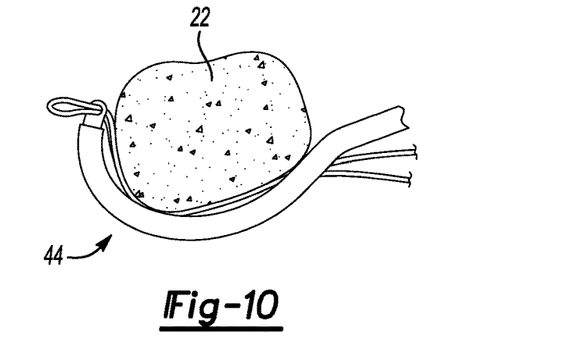
FIG. 10 illustrates the suture passer around the bone and in a first position.
Figure 11:
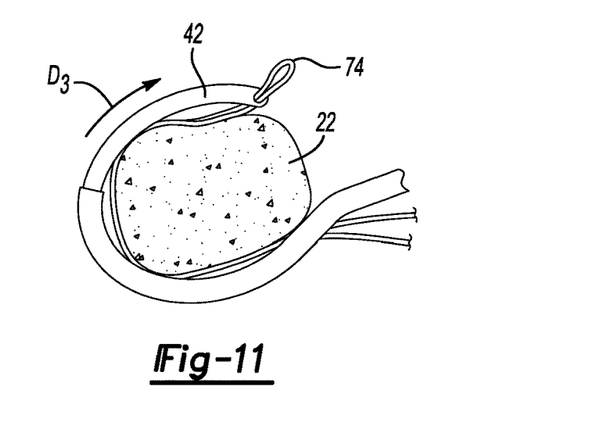
FIG. 11 illustrates the suture passer around the bone and in a second position.

With the folded end 74 placed in the eyelet 48, the distal end 44 of the cannula 40 is maneuvered around a bone 22, as illustrated in FIG. 9, to push the folded end 74 around the bone 22. As the folded end 74 is moved around the bone 22, the free ends 76, 78 are retained in their original position. In the position of FIG. 10, the suture folded end 74 is only partially wrapped around the bone 22. In order to fully wrap the suture 26 around the bone 22, the suture carrier 42 is moved in the direction $D_3$ by distal movement of the actuation member 50 in the direction $D_1$ (see FIG. 1). In FIG. 11, the folded end 74 has been moved to a position where a surgeon, for example, can grasp the folded end, completing the first wrap around the bone 22. Again, in this example, the suture 26 is folded. Thus, the first wrap includes a wrapping of both the first and second lengths 75, 77 of suture.

Figure 12:
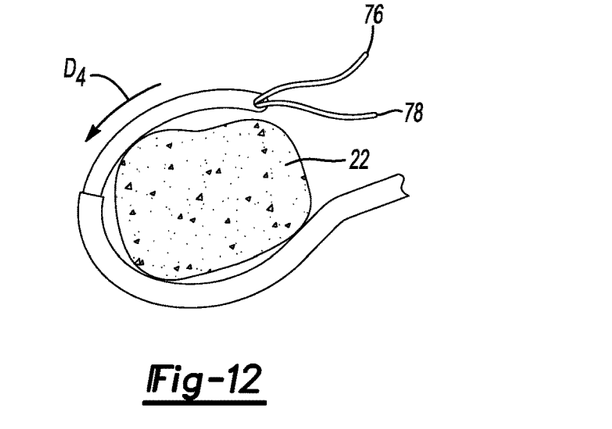
FIG. 12 illustrates an example method step of inserting free ends of suture into an eyelet of the suture passer.
Figure 13:
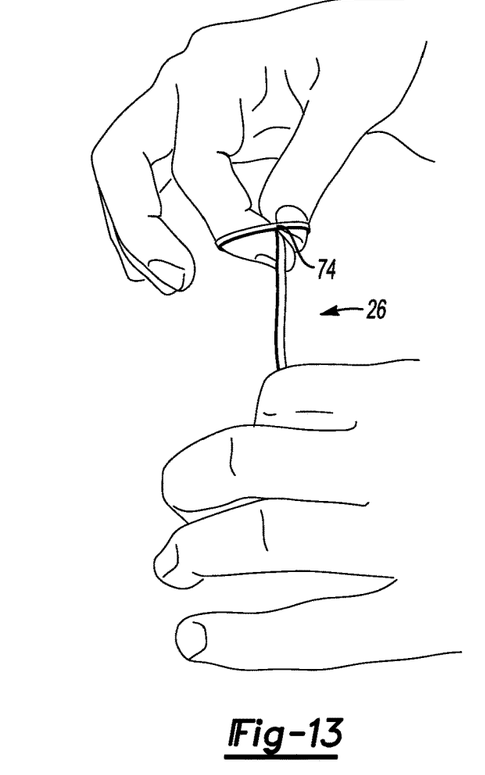
FIG. 13 illustrates an example method step of tying a sliding knot, and in particular illustrates an eyelet being formed by the folded end of suture.

Next, the surgeon maintains the position of the folded end 74, which has been wrapped around the bone, and feeds the two free ends 76, 78, which are still in their original position, through the eyelet 48, as illustrated in FIG. 12. Then, the suture carrier 42 is moved in the direction $D_4$ to draw the free ends 76, 78 of suture back toward the cannula 40. Then, the suture passer 36 is maneuvered to pull the free ends 76, 78 back around the bone 22.

By wrapping the folded end 74 around the bone in a first direction while maintaining the position of the free ends 76, 78, and then wrapping the free ends 76, 78 about the bone in a second, opposite direction while maintaining the position of the folded end 74, the result is a single piece of folded suture that has been wrapped around the bone twice. Further, because the suture 26 is folded, the above technique provides a cerclage having the effective width of the four pieces of suture, which increases the coverage and effectiveness of the suture wrap cerclage 20.

Further, the above technique only requires a suture passer to be maneuvered around the bone and removed once, which reduces the time required to wrap the suture and reduces risk of further injury to adjacent soft tissue during surgery. While the suture 26 is wrapped around the bone 22 twice in the above example, the suture 26 could be wrapped only once or additional times depending on the severity of the fracture, for example.

Figures 14, 14A:
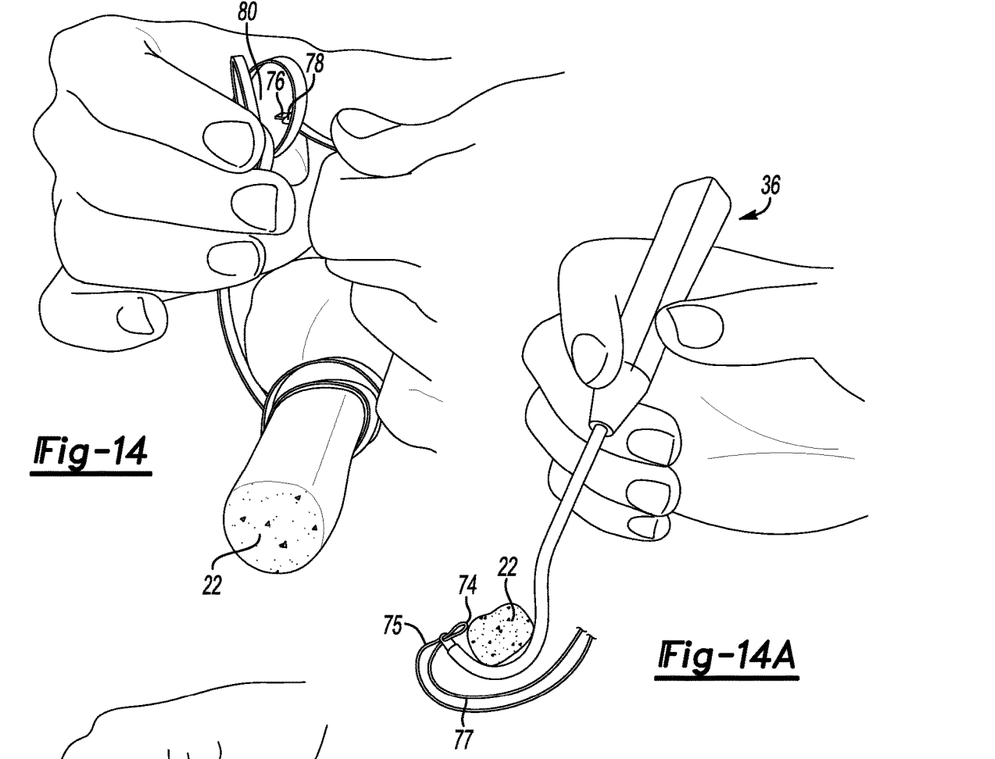
FIG. 14 illustrates an example method step of tying a sliding knot, and in particular illustrates the free ends of suture being placed through the eyelet.
FIG. 14A illustrates an example method step of maneuvering the suture passer around bone.
Figure 14B:
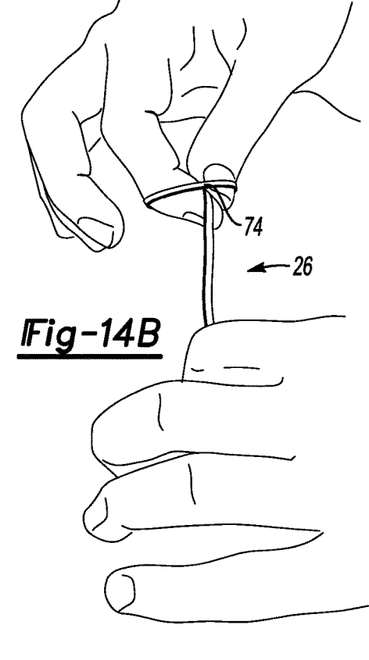
FIG. 14B illustrates an example method step of tying a sliding knot, and in particular illustrates an eyelet being formed by the folded suture.
Figure 14C:
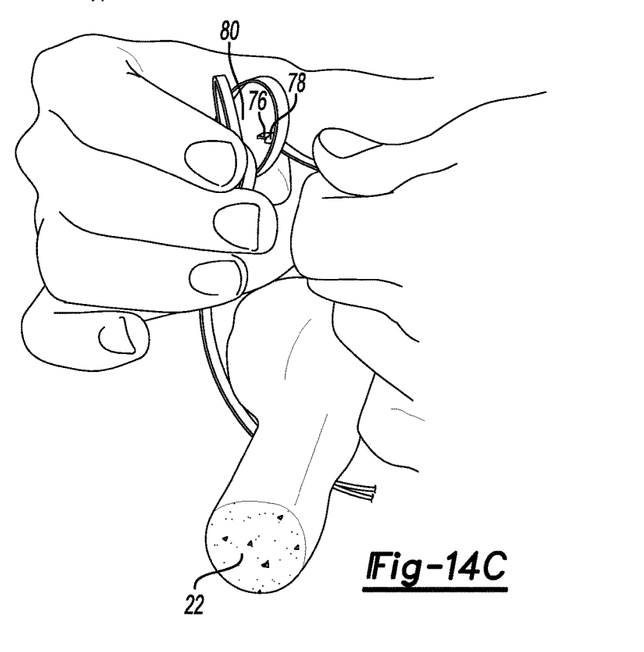
FIG. 14C illustrates an example method step of tying a sliding knot relative to suture that has been wrapped around bone only once.

Once wrapped around the bone 22, the suture 26 is then secured to the bone. In one example, a sliding knot is provided between the folded end 74 and the first and second free ends 76, 78. To provide the sliding knot, the folded end 74 is folded over an adjacent portion of the lengths 75, 77 (FIG. 13) to provide an eyelet 80 (FIG. 14). FIGS. 14A-14C illustrate an example in which the suture 26 is wrapped around the bone 22 only once. In FIG. 14A, for example, the folded end 74 is passed around the bone as substantially described relative to FIGS. 9-11. In FIG. 14B, the folded end 74 is then folded over an adjacent portion of the lengths to provide an eyelet 80 (FIG. 14C). Regardless of the number of times the suture 26 is wrapped around the bone 22, the first and second free ends 76, 78 are then fed through the eyelet 80 to provide a sliding knot 81 (FIG. 15), which is tightened by hand against the bone 22.

Figure 14D:
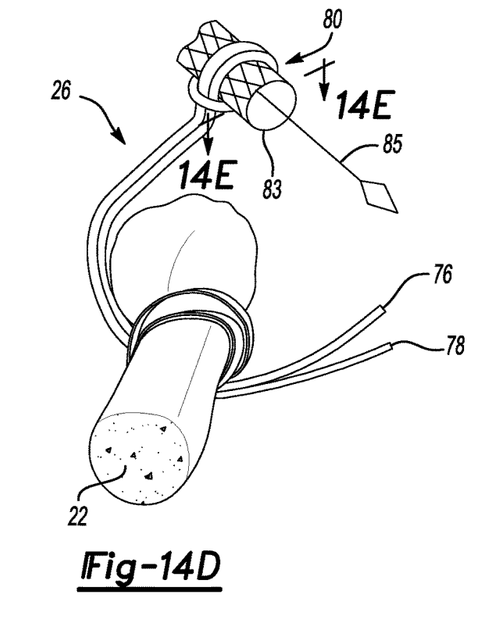
FIG. 14D illustrates a partially pre-tied knot including an eyelet provided within a sheath.

Alternatively, the sliding knot 81 could be partially pre-tied. In particular, the eyelet 80 could be provided within a sheath 83, as illustrated in FIG. 14D. In this example, a sheath 83 of suture material is connected adjacent the folded end 74 prior to surgery such that a surgeon, for example, does not have to fold the suture and form the eyelet 80 during surgery. The sheath 83 in this example is substantially cylindrical, and is formed of a mesh-like suture material. In one example, suture is used to stitch the sheath 83 to the lengths 75, 77 to maintain the eyelet 80. A suture shuttle 85 may be used to pass the free ends 76, 78 through the sheath 83. Once suture is passed through the sheath 83, the sliding knot 81 can be tightened as substantially shown in FIG. 15.

Figure 14E:
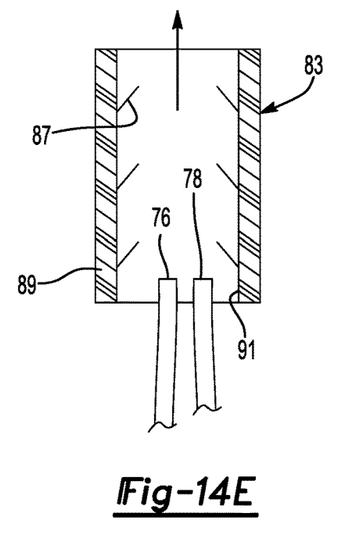
FIG. 14E is a cross-sectional view of the sheath of FIG. 14D.
Figure 15:
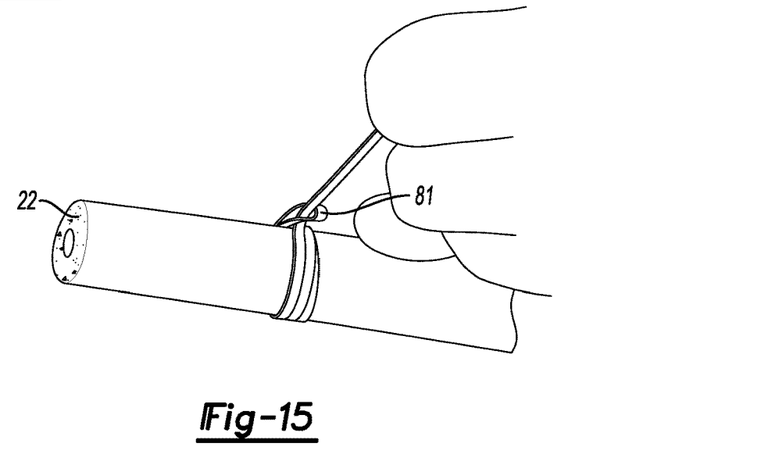
FIG. 15 illustrates an example method step of tying a sliding knot, and in particular illustrates tightening the sliding knot relative to the bone.

Further, as illustrated in FIG. 14E, the sheath 83 may include one or more barbs 87 extending inwardly from a wall 89 of the sheath 83. The barbs 87 in this example are provided by a suture material and are inclined away from a sheath inlet 91. The barbs 87 are configured to engage the suture passing through the sheath 83. For example, when the sliding knot 81 is tightened, the sheath 83 essentially collapses against the suture within the sheath. In this way, the barbs 87 are configured to allow suture to pass into through the sheath inlet 91, while resisting removal of the suture from the sheath 83. The barbs 87 are optional and are not required in all examples.

Figure 16:
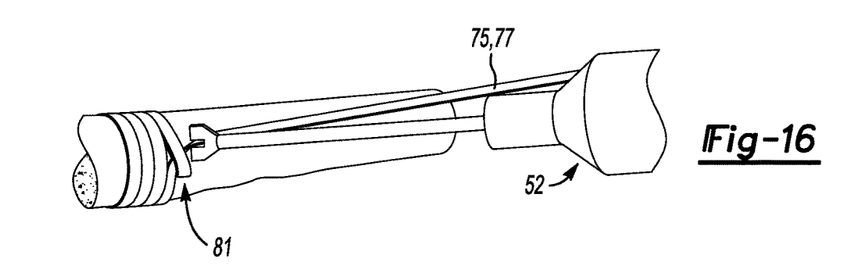
FIG. 16 illustrates an example method step of tensioning the sliding knot using a tensioner.

The sliding knot 81 is then tensioned. In this example, tension is applied by wrapping the first and second free ends 76, 78 around the spool 60 of the suture tensioner 52, and rotating the adjustment wheel 58 until the desired tension is reached, as generally illustrated in FIG. 16. Finally, at least one knot is tied between the first and second free ends 76, 78 to hold the position and tension of the sliding knot 81. In one example, the first and second lengths 75, 77 are tied into at least one half-hitch knot, which essentially "backs up" the sliding knot 81. Other types of locking knots come within the scope of this disclosure.

The result is a suture wrap cerclage 20, as substantially illustrated in FIG. 1, which supports a fractured bone under tension, and does so without implanting any metallic components into the body, and without requiring any structural changes (such as drilling or cutting) the bone 22. Further, the disclosed technique allows surgeons to provide the suture wrap cerclage efficiently and in a manner that is reliable and repeatable. While the method describes how to provide a single suture wrap cerclage 20, more severe fractures may require more than one suture wrap cerclage 20 provided along the length of the bone. In those instances, the benefits provided by this disclosure are even more apparent.

In the above-described method, the suture wrap cerclage is provided by tying at least one knot, and without implanting any structure in the body, with the exception of the suture 26. Other aspects of this disclosure, however, are "knotless," meaning the securing step includes securing the suture 26 to the bone 22 without tying any knots.

Figures 17, 18, 19:
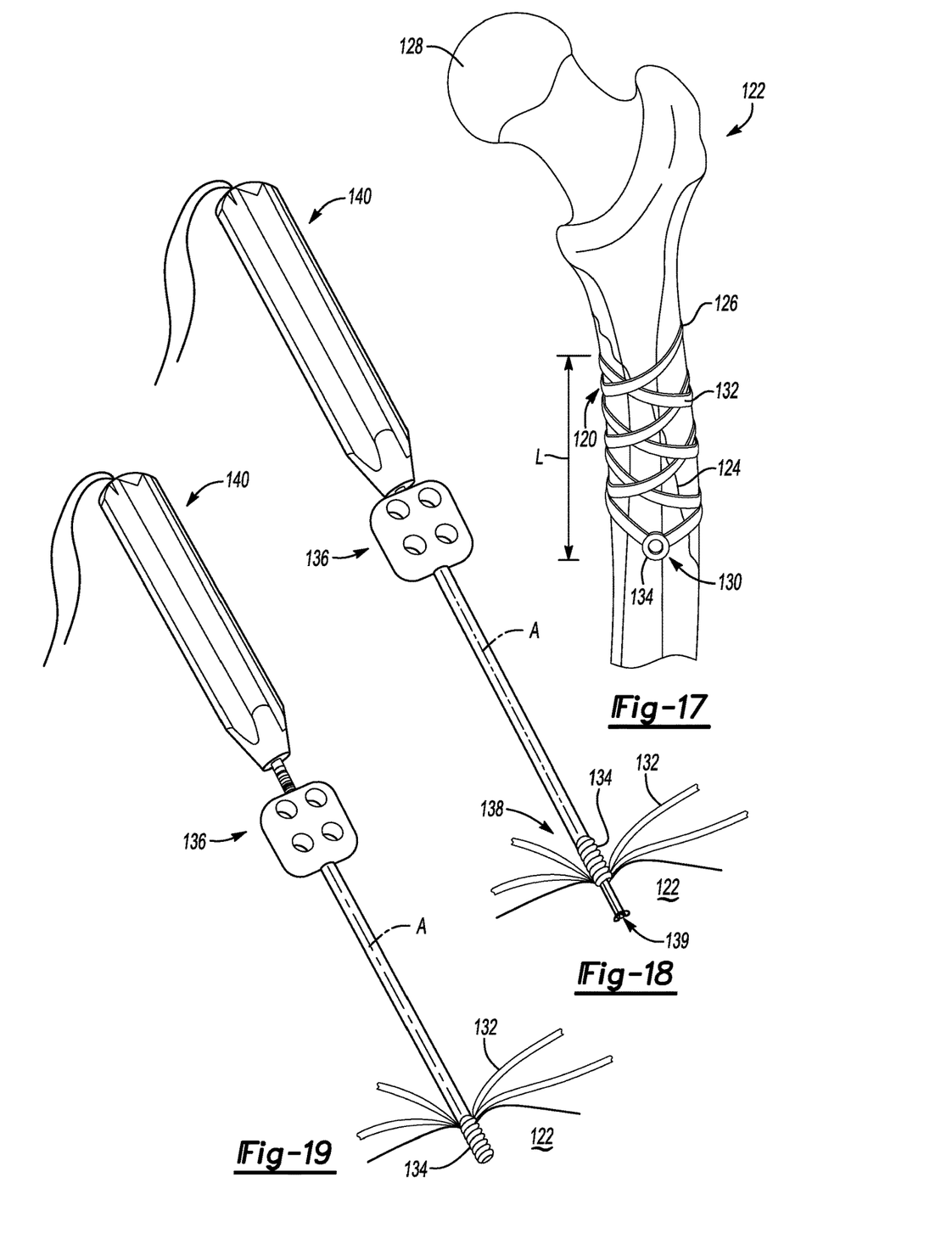
FIG. 17 illustrates a fractured bone having another example suture wrap cerclage.
FIG. 18 illustrates an example inserter in a first position.
FIG. 19 illustrates an example inserter in a second position.

One example knotless arrangement is shown in FIG. 17. In FIG. 17, a suture wrap cerclage 120 is provided around a bone 122, which in this example is a femur, having a fracture 124. The suture wrap cerclage 120 is first wrapped around the bone 122 at a first location 126, adjacent a head 128 of the bone 122, and travels along a length L of the bone to a second location 130, which is spaced-apart from the first location 126, adjacent the condyles of the bone 122, for example.

In the example of FIG. 17, the suture 132 providing the suture wrap cerclage 120 may be wrapped around the bone 122 using a suture passer similar to the suture passer 36 described above. The suture 132 is secured to bone at the second location 130 by a knotless suture anchor 134, using, for example, Arthrex's SwiveLock® or PushLock®.

In general, the knotless suture anchor 134 is positioned by an inserter 136 (FIG. 18) including a distal end 138, a proximal end 140, and a longitudinal axis A between the distal end 138 and the proximal end 140. A first member including an eyelet 139 (such as an eyelet formed by a folded end of suture or a hard eyelet provided by an implant) is oriented to thread the suture 132 across the longitudinal axis A. Further, the first member is situated near the distal end 138 of the inserter and is configured to be placed in bone 122. A second member, which in one example is the anchor 134, is situated near the distal end 138 of the inserter 136. The second member 134 is moveable, by a portion of the inserter 136, relative to the first member in a distal direction toward the eyelet into a suture securing position where the second member 134 locks the suture 132 in place, as shown in FIG. 19. Again, while one example has been described, other knotless anchors come within the scope of this disclosure.

Figure 20:
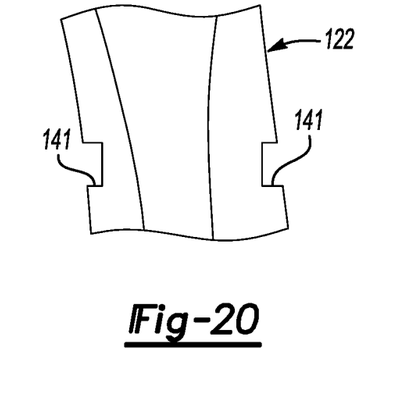
FIG. 20 illustrates a first example suture-retaining feature.
Figure 21:
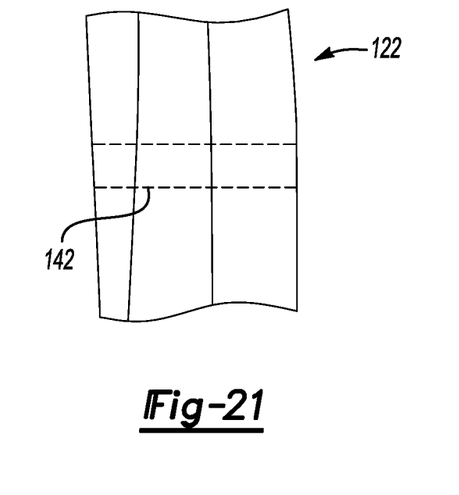
FIG. 21 illustrates a second example suture-retaining feature.

In some examples, the bone 122 may be machined to prevent slippage of the suture 132 from the first location 126 to the second location 130. In one example, illustrated in FIG. 20, the bone 122 may be provided with one or more notches 141 adjacent the first location 126, which are configured receive the suture 132. In another example, illustrated in FIG. 21, the bone 122 may be provided with a through-hole 142 (shown in phantom) adjacent the first location 126, through which the suture 132 may be fed. The notches 141 and through-hole 142 are only examples. Other types of suture-retaining features come within the scope of this disclosure. It should be understood that the suture-retaining features can be formed using conventional bone machining techniques, such as cutting or drilling.

Figure 22:
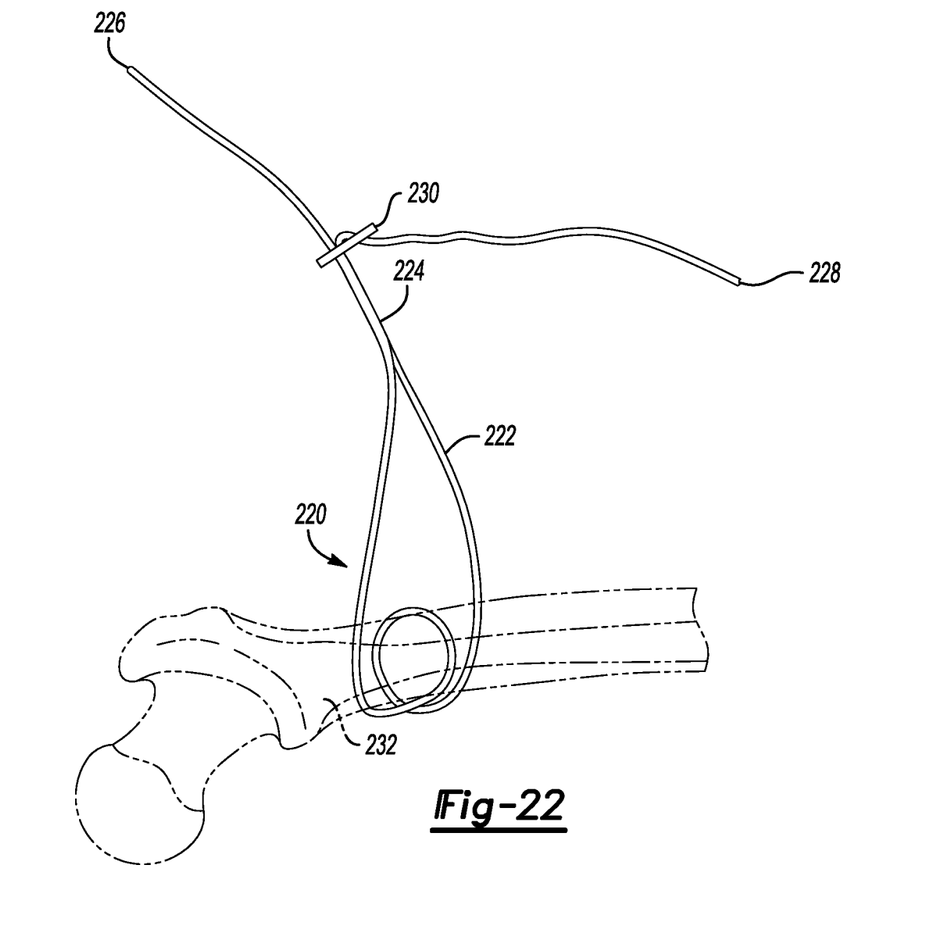
FIG. 22 illustrates a fractured bone having another example suture wrap cerclage.

FIG. 22 is another example securing technique that does not involve tying knots. In the example of FIG. 22, the suture wrap cerclage 220 is provided by a self-cinching suture 222 including at least one splice 224. An example type of self-cinching suture is included in Arthrex's TightRope®, which is a suture-button construct.

In general, the self-cinching suture 222 includes a first end 226, a second end 228, the splice 224, and a fixation device 230 (sometimes referred to as a "button"). In an example method, the second end 228 of the self-cinching suture is wrapped around a bone 232 one or more times (here, twice), and fed through the splice 224. In this example, the second end 228 is also fed through the fixation device 230. The second end 228 may be wrapped around the bone 232 using the above-discussed techniques.

Once wrapped, the second end 228 is pulled relative to the first end 226, which tightens the self-cinching suture 222 and cinches the suture 222 against the bone 232 to provide a suture wrap cerclage. Once tightened, the fixation device 230 maintains the position of the suture 222 relative to the bone 232. While one example self-cinching suture has been described, other types of self-cinching sutures come within the scope of this disclosure.

Figures 23, 24, 25, 26:
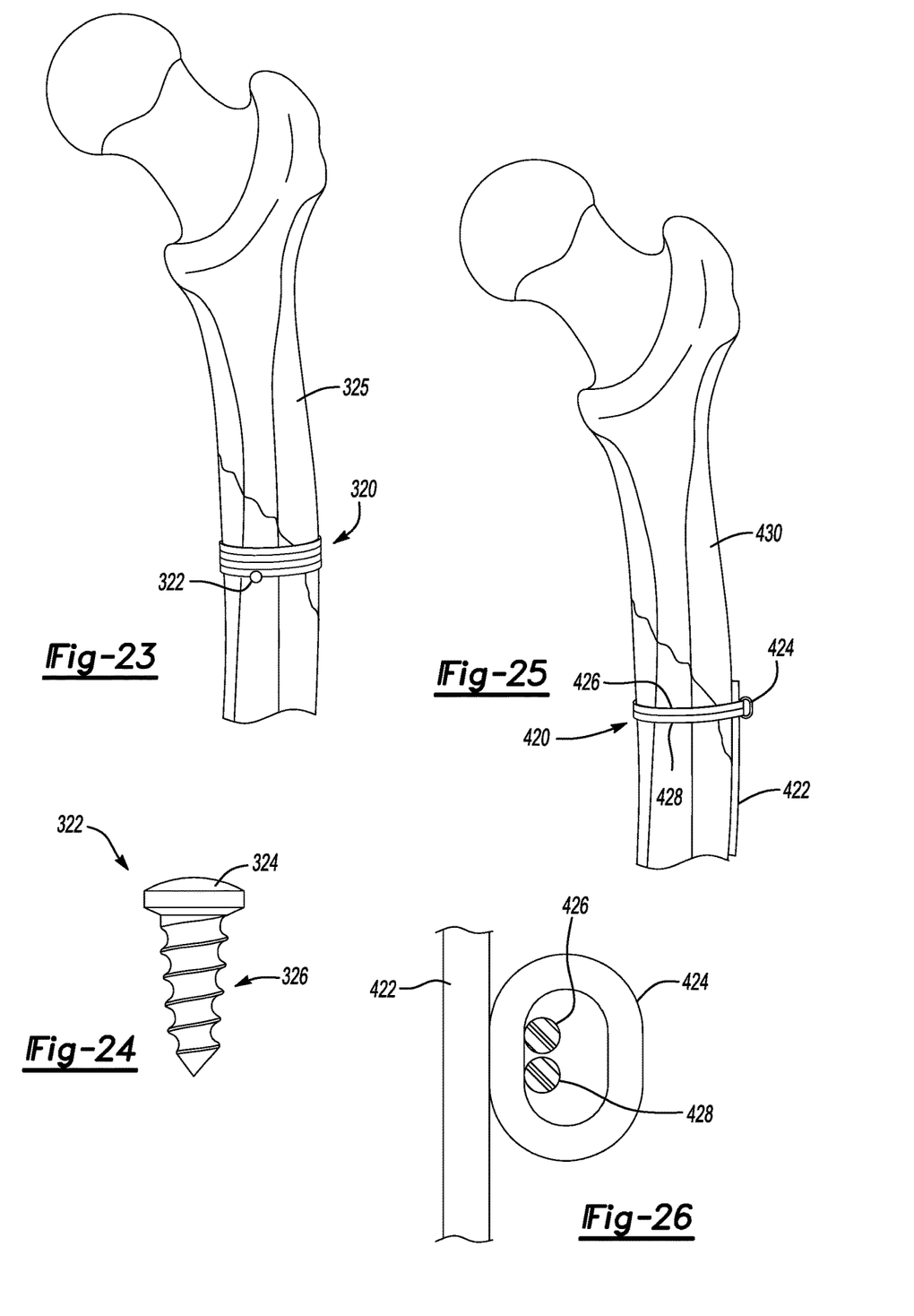
FIG. 23 illustrates a fractured bone having an example suture wrap cerclage, which is held in place using a bone screw.
FIG. 24 illustrates the detail of an example bone screw.
FIG. 25 illustrates a fractured bone having an example suture wrap cerclage, which is held in place using a bone plate.
FIG. 26 illustrates an eyelet of the bone plate.

FIGS. 23-24 illustrate yet another suture securing technique. In FIG. 23, a suture wrap cerclage 320 is held in place, at least in part, by a bone screw 322. An example bone screw 322 is illustrated in FIG. 24. As illustrated, the bone screw 322 includes a head 324 and a threaded shank 326. The head 324 in this example is sized to hold suture between the head 324 and bone 328. The bone screw 322 can be placed in a location adjacent an expected location of the suture wrap cerclage 320. In the illustrated example, the bone screw 322 is placed below an expected location of the suture wrap cerclage 320.

In FIG. 23, for example, the bone screw 322 is inserted partially into bone 328. Then, the suture providing the suture wrap cerclage 320 is wrapped about the bone per any of the above techniques. During wrapping, the bone screw 322 holds a position of the suture and prevents slippage of the suture. Once wrapped, the bone screw 322 can be tightened. When tightened, the bone screw 322—specifically the head 324—secures at least one length of suture to bone, which helps maintain the position of the suture warp cerclage 320.

Another example suture wrap cerclage 420 is illustrated in FIGS. 25-26. In FIG. 26, the suture wrap cerclage 420 is provided relative to a bone plate 422 which includes an eyelet 424. The bone plate 422 may be fixed to the bone at one or more locations along its length. The eyelet 424, as perhaps best seen in FIG. 26, is fixed to the bone plate 422 and is configured to hold strands 426, 428 of suture in place relative to bone 430. The suture wrap cerclage 420 can be wrapped using any of the above techniques with the exception that, in this example, the strands 426, 428 pass through the eyelet. The eyelet 424 thus prevents slippage and substantially maintains a position of the suture wrap cerclage 420.

Figure 27:
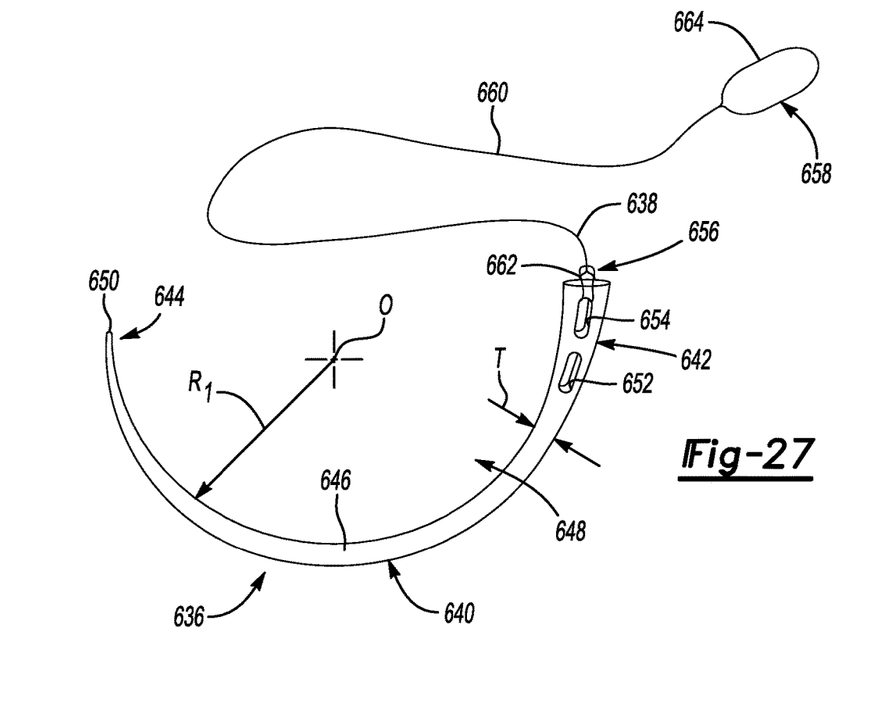
FIG. 27 illustrates another example suture passer including a curved needle and shuttling suture.

FIG. 27 illustrates another example suture passer 636. In this example, the suture passer 636 is used in combination with a shuttling suture 638, which assists in wrapping suture around bone, as will be discussed below. Before getting to the method of use, the suture passer 636 in this example is provided by a curved needle 640. The curved needle 640 in this example has a proximal end 642, a distal end 644, and a main body portion 646 extending between the proximal end 642 and the distal end 644. In this example, the curved needle 640 is curved such that it follows a constant radius $R_1$ having an origin O in an expected bone location 648. The radius $R_1$ in this example corresponds to the expected contour of a bone.

In this example, the main body portion 646 includes a thickness T tapering from the proximal end 642 to the distal end 644. A tip 650 of the distal end 644 is blunt in one example. In another example, the tip 650 is sharpened.

At the proximal end 642, the suture passer 636 includes two eyelets 652, 654. Both the first and second eyelets 652, 654 are configured to receive suture. In this example, the second eyelet 654 is proximal to the first eyelet 652 and receives the shuttling suture 638.

The shuttling suture 638 includes a first end 656, a second end 658, and a length 660 between the ends 656, 658. The first and second ends 656, 658 include closed loops 662, 664, respectively. The closed loops 662, 664 are configured to receive suture and shuttle the suture between locations. The shuttling suture 638 may be provided by a nitinol wire material in some examples. This disclosure is not limited to nitinol wire, however. The shuttling suture 638 may be used to wrap suture around bone without requiring the suture passer to be backed-out around the bone, as in the method of FIGS. 7A-16 for example.

Figure 28:
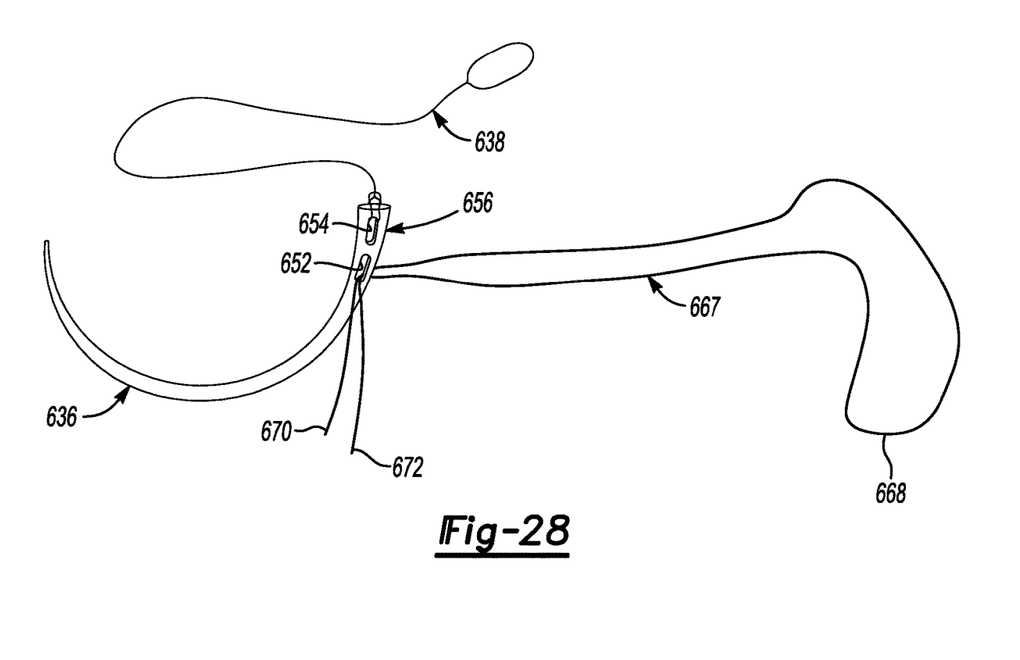
FIG. 28 illustrates the suture passer of FIG. 27 with free ends of a piece of suture received in an eyelet of the suture passer.

FIGS. 28-33 illustrate an example method of using the suture passer 636 and the shuttling suture 638. In FIG. 28, a piece of suture 667 is folded in half about its length to provide a folded end 668 and first and second free ends 670, 672. The suture 667 is a high strength braided suture, such as Arthrex, Inc.'s FiberTape™, in one example. In this example, the first and second free ends 670, 672 are received in the first eyelet 652 of the suture passer 636. Further, the first end 656 of the shuttling suture is looped through the second eyelet 654 and pulled against the suture passer 636.

Figures 29, 30, 31:
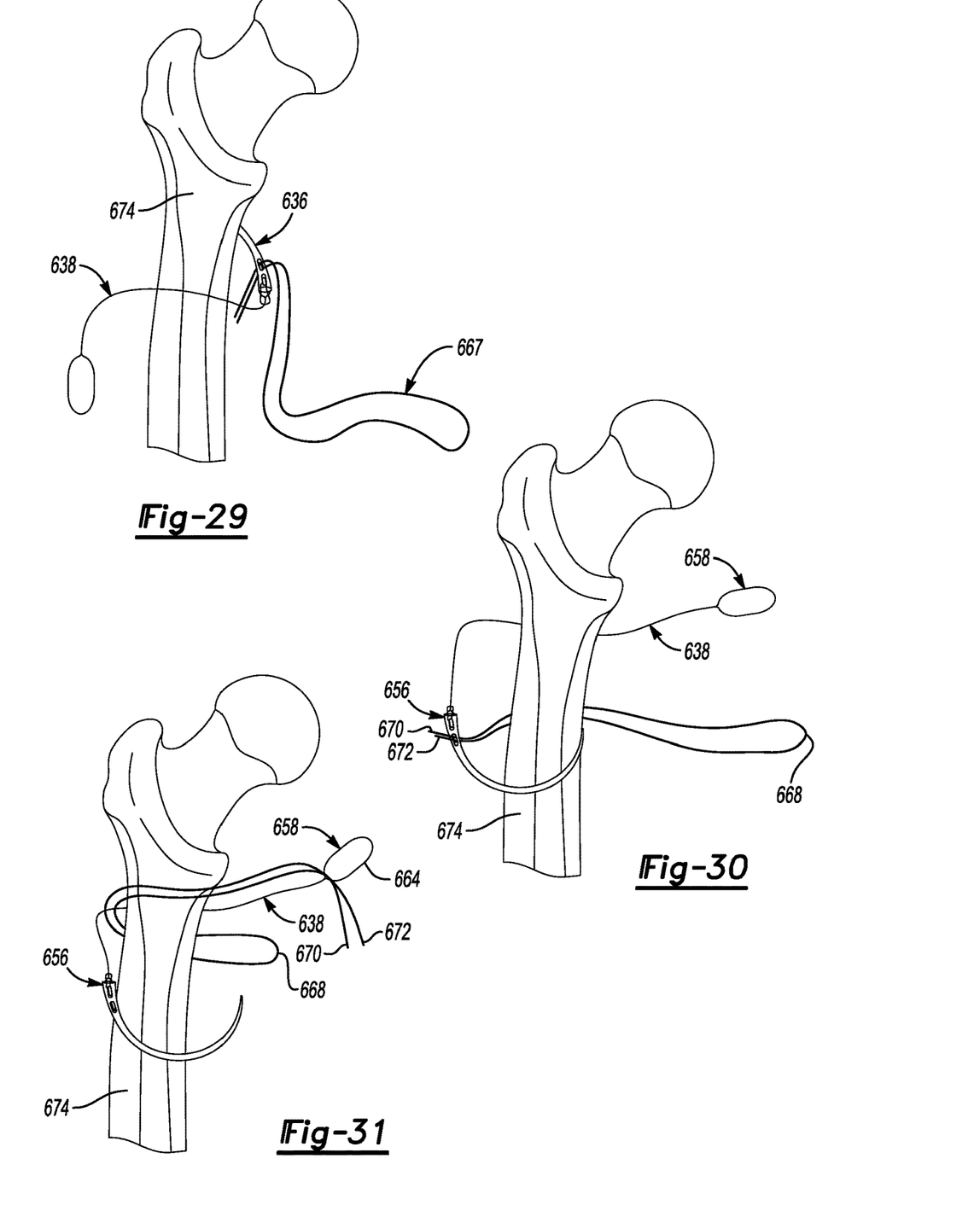
FIG. 29 illustrates an example method step of maneuvering the suture passer of FIG. 27 around bone.
FIG. 30 illustrates another example method step of maneuvering the suture passer of FIG. 27 around bone.
FIG. 31 illustrates another example method step of providing the free ends of the suture in a loop of the shuttling suture.

With the suture 667 and shuttling suture 638 received in the first and second eyelets 652, 654, respectively, the suture passer 636 is maneuvered around bone 674, as illustrated in FIG. 29. The suture passer 636 is pushed partially around the bone 674 in a first direction to the position generally illustrated in FIG. 29. The suture passer 636 is then pulled around bone in the first direction to complete a first wrap of the suture 667 around the bone 674, as illustrated in FIG. 30. In one example, a surgeon retrieves and pulls the suture passer 636 by engaging the distal end 644 of the suture passer 636 with a surgical device.

In FIG. 30, the first and second free ends 670, 672 of the suture 667 have been passed around the bone 674, while the folded end 668 has not been passed around the bone 674. Further, the first end 656 of the shuttling suture 638 has been wrapped around the bone 674, while the second end 658 has not.

Figure 32:
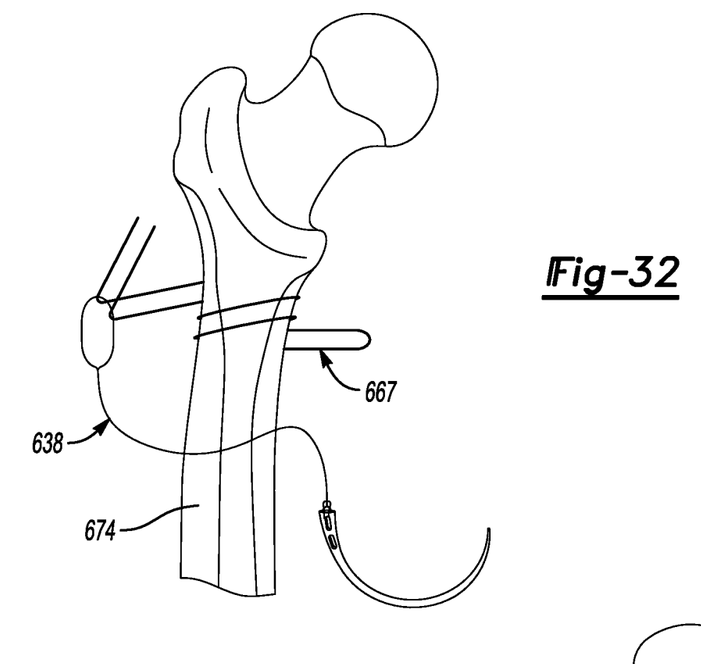
FIG. 32 illustrates another example method step of pulling the shuttling suture around bone.

To wrap the suture 667 around the bone 674 a second time, the free ends 670, 672 are loaded into the loop 664 at the second end 658 of the shuttling suture 638, as illustrated in FIG. 31. Then, the shuttling suture 638 is pulled around the bone 674 in the first direction, as illustrated in FIG. 32. The result is a piece of folded suture wrapped twice around bone. The result requires only one pass of a suture passer 636 around the bone, and one pass of a shuttling suture around the bone. The suture passer 636 does not need to be backed-out around the bone in a direction opposite the first direction. Pulling the shuttling suture 638 around the bone 674 is perhaps less invasive than backing-out the suture passer, as in some of the previously discussed examples.

Figure 33:
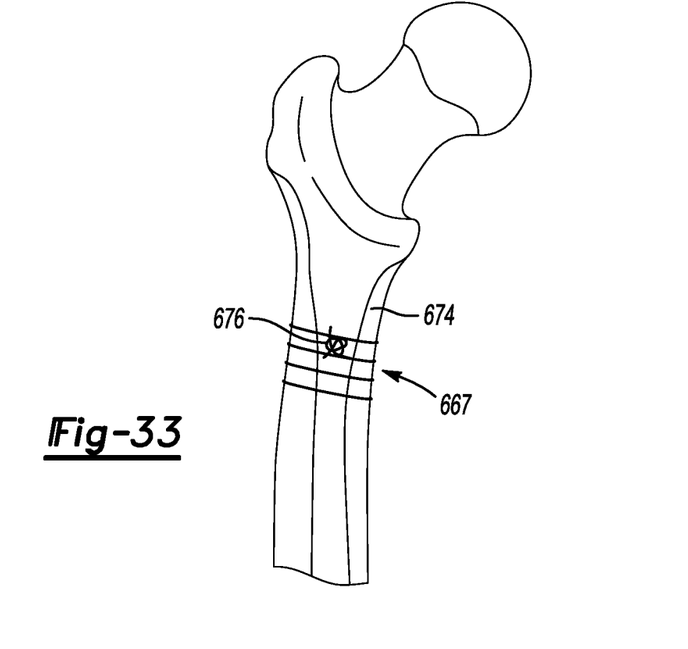
FIG. 33 illustrates an example method step of tying a knot to secure the suture to bone.

Finally, the suture 667 is secured to the bone 674 using any one of the above techniques. In the example of FIG. 33, the suture 667 is secured to the bone 674 by tying a knot 676.

It should be understood that the example of FIGS. 27-33 could be combined with any of the above techniques, including being used in combination with the tensioner 52, the knotless suture anchor 134, or the techniques associated with FIGS. 20-26, for example.

The suture wrap cerclages of this disclosure provide a reliable and effective bone cerclage, which promotes healing of fractured bones. Further, the disclosed methods and systems allow surgeons to provide suture wrap cerclages in an efficient manner without sacrificing consistency or quality.

It should be understood that terms such as "proximal" and "distal" are used consistent with their art-accepted meaning. These terms should not otherwise be considered limiting.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A method for providing a bone cerclage, comprising:
wrapping suture around a bone at least twice;
tensioning the suture to tighten the suture relative to the bone; and
securing the suture to the bone.

2. The method as recited in claim 1, wherein the securing step includes securing the suture to the bone by tying a knot.

3. The method as recited in claim 2, wherein the securing step includes providing a sliding knot between a folded end of the suture and first and second free ends of the suture.

4. The method as recited in claim 3, wherein the sliding knot is at least partially pre-tied.

5. The method as recited in claim 3, wherein the tensioning step includes using a tensioner to pull the first and second ends relative to the sliding knot to tighten the suture.

6. The method as recited in claim 1, wherein the wrapping step includes wrapping the suture around the bone a first time in a first direction and a second time in a second direction opposite the first direction.

7. The method as recited in claim 6, wherein the suture is wrapped around the bone the first time by wrapping first and second free ends of the suture around the bone in the first direction.

8. The method as recited in claim 7, wherein the suture is wrapped around the bone the second time by providing wrapping the first and second free ends around the bone in the second direction.

9. The method as recited in claim 1, wherein the wrapping step includes using a suture passer to wrap the suture around the bone.

10. The method as recited in claim 9, wherein the suture passer is a needle.

11. The method as recited in claim 10, wherein the needle is a curved needle.

12. The method as recited in claim 11, wherein the needle includes a proximal end, a distal end, and a main body portion having a thickness tapering between the proximal end and the distal end.

13. The method as recited in claim 10, wherein a tip of needle is blunt.

14. The method as recited in claim 10, wherein a tip of the needle is sharpened.

15. The method as recited in claim 1, wherein the suture is a folded piece of suture.

16. A method for providing a bone cerclage, comprising:
wrapping a piece of suture around bone a first time in a first direction;
wrapping the suture around bone a second time in a second direction opposite the first direction;
tensioning the suture to tighten the suture relative to the bone; and
securing the suture to the bone by tying a knot.

17. The method as recited in claim 16, wherein the securing step includes providing a sliding knot between a folded end of the suture and first and second free ends of the suture.

18. The method as recited in claim 17, wherein the tensioning step includes using a tensioner to pull the first and second ends relative to the sliding knot to tighten the suture.

19. The method as recited in claim 16, wherein:
the suture is wrapped around the bone the first time by wrapping first and second free ends of the suture around the bone in the first direction;
the suture is wrapped around the bone the second time by providing wrapping the first and second free ends around the bone in the second direction.

20. The method as recited in claim 16, wherein the wrapping step includes using a needle to wrap the suture around the bone.

* * * * *